United States Patent [19]

Kurusu et al.

[11] Patent Number: 5,844,112
[45] Date of Patent: Dec. 1, 1998

[54] METHOD FOR THE PREPARATION OF (METH)ACRYLONITRILES

[75] Inventors: Akira Kurusu; Nobuji Kishimoto; Isao Nakamura; Etsushige Matsunami, all of Suita, Japan

[73] Assignee: Nippon Shokubai Co., Ltd., Osaka, Japan

[21] Appl. No.: 666,577

[22] PCT Filed: Jan. 22, 1996

[86] PCT No.: PCT/JP96/00096

§ 371 Date: Jul. 1, 1996

§ 102(e) Date: Jul. 1, 1996

[51] Int. Cl.$^6$ .................................................. C07C 253/26
[52] U.S. Cl. ............................................................ 558/319
[58] Field of Search .............................................. 558/319

[56] References Cited

U.S. PATENT DOCUMENTS

| 5,008,427 | 4/1991 | Brazdil, Jr. et al. | 558/319 |
| 5,093,299 | 3/1992 | Suresh et al. | 502/212 |

Primary Examiner—Joseph McKane
Assistant Examiner—Ebenezer Sackey
Attorney, Agent, or Firm—Sherman and Shalloway

[57] ABSTRACT

A method for the preparation of (meth)acrylonitriles following ammoxidation process comprising catalytically oxidizing at least one saturated hydrocarbon selected from the group consisting of propane and isobutane with a mixed gas containing mole-cular oxygen and ammonia in the presence of a catalyst, is provided, the method being characterized by the use of a catalyst composed of complex oxide which is expressed by the general formula (I) below:

$$Cr\alpha Sb\beta W\gamma Ox \qquad (I)$$

(in which $\alpha$, $\beta$ and $\gamma$ denote the number of atoms of Cr, Sb and W, respectively, and when $\alpha$ is 1, $\beta$ is 0.5–5 and $\gamma$ is 0.2–2; and x is a value determined by valence of the existing elements).

According to this method, the object nitriles can be prepared at high yields with industrial advantages.

2 Claims, No Drawings

METHOD FOR THE PREPARATION OF (METH)ACRYLONITRILES

This application is a 371 of PCT/JP96/000096 filed on Jan. 22, 1996.

TECHNICAL FIELD

This invention relates to a process for the preparation of (meth)acrylonitriles by ammoxidation of at least one saturated hydrocarbon selected from the group consisting of propane and isobutane, in which the hydrocarbon is contacted with molecular oxygen and ammonia in the vapor phase.

TECHNOLOGICAL BACKGROUND (Meth)acrylonitriles have been manufactured in large quantities, as the intermediates for a great variety of industrial products represented by synthetic fibers and synthetic resins. As a conventional production process thereof, ammoxidation is generally known, in which olefinic starting materials, i.e., propylene, isobutene, and the like, are contacted with molecular oxygen and ammonia in the vapor phase, in the presence of a catalyst.

Whereas, with the recent rise in olefin price, development of processes for making the various derivatives which have heretofore been manufactured from olefins, using as the starting materials less expensive paraffins, comes to draw attention. As the catalyst systems used for the production of (meth)acrylonitriles from propane or isobutane by "ammoxidation" process, Sb—U oxide catalyst [Japanese Patent Publication (Kokoku) No. 14371/1972], Sb—Sn oxide catalyst (Kokoku No. 28940/1975), V—Sb oxide catalyst [Japanese Laid-open (Kokai) Nos. 33783/1972, 268668/1989, 95439/1990 and 261544/1990], Bi—Mo oxide catalyst (Kokai No. 16887/1973, Kokoku No. 42071/1980, and Kokai No. 157356/1991], V—P oxide catalyst (Kokoku No. 5188/83), Bi—V oxide catalyst (Kokai No. 295545/1988), etc. are known. Still recently, furthermore, patent applications have been made for V—Sn—Sb—Cu oxide catalyst (Kokai No. 275266/1992), Mo—V—Te—Nb oxide catalyst (Kokai No. 257/1990), Ag—Bi—V—Mo oxide catalyst (Kokai No. 58961/1991), Ga—Bi—Mo or Ta—Bi—Mo oxide catalyst (Kokai No. 58962/1991), Mo—Ta or Mo—Nb oxide catalyst (Kokai No. 213849/1993), etc. Also mixed catalyst systems of a number of above catalyst systems with those having olefin-ammoxidation ability have been proposed (Kokai Nos. 295546/1988, 38051/1989, 17159/1990, 43949/1990, 75347/1990, 111444/1990 and 258065/1990).

Of these methods, those of adding a minor amount of a halide to the reaction systems as a promotor give the nitriles, which are the intended reaction products, at relatively high yield. However, such methods are difficult of industrial practice because of the corrosion problem of the reaction equipments which incurs restrictions on the construction materials of the equipments. On the other hand, methods not using any promotor give only low yield of nitrites and have not reached an industrially practiceable level.

DISCLOSURE OF THE INVENTION

Accordingly, therefore, the object of the present invention resides in provision of a method which is free of those defects in the conventional methods and which enables production of (meth)acrylonitriles at high yields and with industrial advantages.

We have made concentrative studies on production of (meth)acrylonitriles by ammoxidation process in which at least one saturated hydrocarbon selected from the group consisting of propane and isobutane is contacted with a mixed gas comprising molecular oxygen and ammonia in the vapor phase in the presence of a catalyst, to discover that nitrile yields higher than those obtainable in conventional methods can be achieved by use of a catalyst composed of a complex oxide containing oxides of three elements of chromium, antimony and tungsten as the essential components, which is supported on a refractory inorganic carrier, if necessary, and completed the present invention.

Thus, according to the invention a process is provided which comprises preparation of (meth)acrylonitriles by catalytically oxidizing propane and/or isobutane in the vapor phase, with molecular oxygen and ammonia in the presence of a catalyst, said process being characterized by use of a catalyst composed of a complex oxide which is expressed by the general formula (I) below:

$$Cr\alpha Sb\beta W\gamma Ox \qquad (I)$$

(in which $\alpha$, $\beta$ and $\gamma$ denote the numbers of atoms of Cr, Sb and W, respectively, where, when $\alpha$ is 1, $\beta$ is 0.5–5 and $\gamma$ is 0.2–2; and x is a value determined by valence of the existing elements).

Among the complex oxides expressed by above general formula (I), particularly those of the composition in which $\alpha$ is 1, $\beta$ is 1 to 3 and $\gamma$ is 0.5–1.5 give the intended nitrites at high yields.

It is furthermore preferred, according to the present invention, to use a catalyst composed of a complex oxide which contains, concurrently with the elements composing the complex oxide as expressed by above general formula (I), at least one element selected from the group consisting of Nb, Mo, Mn, Fe, Co and Ni (hereafter they may be referred to as "A group elements") in such an amount that the atomic ratio of A group element(s) to Cr exceeds 0 but not more than 0.1. These catalysts according to the present invention which additionally contain A group elements achieve the effect of improved activity or selectivity. Among the A group elements, Nb is particularly preferred for increasing yield of the object product. It is particularly preferred, furthermore, that the atomic ratio of A group element(s) to Cr is within a range of 0.05 to 0.1.

According to the invention, it is also preferred to use a catalyst composed of a complex oxide which contains, concurrently with the elements composing the complex oxide as expressed by the general formula (I), at least one element selected from the group consisting of V, Nb, Mo, Mn, Fe, Co and Ni (hereafter they may be referred to as "A' group elements") in such an amount that the atomic ratio of the A' group element(s) to Cr exceeds 0 but not more than 0.1 and that to Sb exceeds 0 but not more than 0.04. Among the A' group elements, V or Nb is particularly preferred for increasing the object product. It is particularly preferred that the atomic ratio of the A' group element(s) to Cr is within a range of 0.05 to 0.1, for improving the yield of the object product.

It is particularly preferred to use the catalyst according to the present invention as supported on a refractory inorganic carrier, to improve the activity and physical durability of the catalyst.

As useful refractory inorganic carriers, at least one oxide selected from the group consisting of silica, alumina, titania, zirconia, silica-alumina, silica-titania and silica-zirconia. Of those, silica-alumina is particularly preferred for improving yield of the object product.

Those catalysts useful for the present invention can be prepared by the methods known per se, which are routinely practiced in the technological field pertinent to the invention. For instance, they can be prepared by the steps of: dissolving chromium nitrate in warm water; adding thereto an aqueous solution of ammonium metatungstate (marketed product); further adding antimony trioxide in powder form, and if necessary, an aqueous solution of at least one compound of at least one element selected from the group consisting of V, Nb, Mo, Mn, Fe, Co and Ni, and optionally a carrier such as silica, alumina and the like; mixing them by stirring for a predetermined length of time; heating and concentrating the mixture; drying the resulting slurry; and then calcining the dried slurry at 400°–800° C. The calcination is conducted in open air, while it may be carried out in high or low oxygen concentration. It is preferred to carry out the final calcination step in an atmosphere of low oxygen concentration (1%–15%), for obtaining high catalytic performance.

The materials to be used for preparing the catalyst useful for the invention are subject to no critical limitation, which may be, for example, nitrates, oxides, hydroxides, chlorides, carbonates, acetates, metallic acids, ammonium salts of metallic acids, etc.

As the starting materials of the carriers, besides shaped bodies of alumina, silica, silica-alumina, etc., powder, gel, sol, etc. of oxides or hydroxides can be suitably used in versatile ways according to the form of use of the catalyst.

As the material gases to be subjected to ammoxidation according to this invention, besides propane and/or isobutane, molecular oxygen and ammonia, diluting gases may be used if necessary. As the molecular oxygen source, air or pure oxygen can be used. Preferred molar ratio of molecular oxygen is 0.2–5 times by volume to propane, and that of ammonia is 0.2–3 times by volume to propane. As a diluting gas, an inert gas such as nitrogen, helium, carbon dioxide, etc., and steam or the like is conveniently used.

The vapor phase catalytic ammoxidation reaction according to the present invention can be conveniently practiced by contacting said material gas with said catalyst at a space velocity of 300–5,000 hr$^{-1}$ at a temperature between 300° C.–600° C. Said vapor phase catalytic ammoxidation is normally conducted under normal pressure, but reduced or elevated pressures may be employed. The reaction system is subject to no critical limitation, but any of fixed bed, moving bed or fluidized bed systems can be adopted. Again, either single flow or recycling system is practiceable.

EFFECT OF THE INVENTION

According to the ammoxidation method of the present invention, at least one saturated hydrocarbon selected from the group consisting of propane and isobutane is catalytically oxidized by a mixed gas containing molecular oxygen and ammonia, in the presence of an above-described catalyst containing as the essential components chromium, antimony and tungsten, whereby (meth)acrylonitriles can be prepared at high yields with industrial advantages.

THE BEST EMBODIMENT FOR PRACTICING THE INVENTION

Hereinafter the present invention shall be explained still more specifically, referring to working Examples.

In the following Examples, conversion, one pass yield and selectivity, inclusive of those of side products, are each defined as follows.

When the starting material is propane:

$$\text{Conversion (mol \%)} = \frac{\text{mol number of reacted propane}}{\text{mol number of fed propane}} \times 100$$

Selectivity (mol %) =

$$\frac{\text{mol number of each of formed compounds}}{\text{mol number of reacted propane}} \times$$

$$\frac{\text{carbon number of each compound}}{3} \times 100$$

one pass yield (mol %) =

$$\frac{\text{mol number of each of formed compounds}}{\text{mol number of fed propane}} \times$$

$$\frac{\text{carbon number of each compound}}{3} \times 100$$

When the starting material is isobutane:

$$\text{Conversion (mol \%)} = \frac{\text{mol number of reacted isobutane}}{\text{mol number of fed isobutane}} \times 100$$

Selectivity (mol %) =

$$\frac{\text{mol number of each of formed compounds}}{\text{mol number of reacted isobutane}} \times$$

$$\frac{\text{carbon number of each compound}}{4} \times 100$$

one pass yield (mol %) =

$$\frac{\text{mol number of each of formed compounds}}{\text{mol number of fed isobutane}} \times$$

$$\frac{\text{carbon number of each compound}}{4} \times 100$$

EXAMPLE 1

A 500-ml beaker was charged with 30.2 g of Alumina Sol A-200 (Nissan Chemical Industries; $Al_2O_3$ concentration: 10.5 wt %), 15.5 g of Silica Sol Snowtex N (Nissan Chemical Industries, $SiO_2$ concentration: 20.5 wt %) and 50 ml of water. The contents were stirred under heating, and maintained at about 80° C. Then 24.03 g of chromium nitrate [$(Cr(NO_3)_3 \cdot 9H_2O$, Wako Junyaku, purity: 99.9%] as dissolved in 50 ml of water was added to the beaker, immediately followed by addition of 13.91 g of undiluted aqueous ammonium metatungstate [$(NH_4)_6H_2W_{12}O_{48}$]MW-2 (Nihon Muki-Kagaku Kogyo; containing 50 wt % of $WO_3$). Then 13.14 g of $Sb_2O_3$ (Wako Junyaku, purity: 99.9%) as dispersed in 100 ml of water in a homogenizer was added. The system was maintained at about 80° C. and at the same liquid amount for 2 hours, under stirring. Then the heating temperature was raised to 90° C, and stirring was continued to allow evaporation of the water content. This concentration was conducted for about 3 hours. The resulting paste was dried at 120° C. for 14 hours, and then calcined in open air at 450° C. for 3 hours. Calcination was further conducted in an atmosphere of oxygen concentration 10% (the balance was nitrogen), at 560° C. for 3 hours. Thus obtained catalyst had a composition of: 80 wt % $Cr_1Sb_{1.5}W_{0.5}Ox/10$ wt % $Al_2O_3$–10 wt % $SiO_2$ (in the composition of catalyst as expressed hereafter, the left side of the slash / shows composition of the complex oxide, and the right side, composition of the carrier).

This catalyst was dressed to 9–20 mesh size, and 5 ml thereof was filled in an ordinary flow reactor in which the reaction was conducted. The composition of the reaction gas was $C_3H_8/NH_3/O_2/He/H_2O=1/2/4/7.5/3$ (molar ratio), the space velocity SV employed was 900 hr$^{-1}$, and the reaction temperature was 520° C. The result of the reaction was as shown in Table 1.

EXAMPLE 2

The fed amounts of chromium nitrate, aqueous ammonium metatungstate solution MW-2 and $Sb_2O_3$ were changed to 16.50 g, 19.11 g and 12.03 g, respectively, and a catalyst was prepared by a method otherwise identical with the one employed in Example 1, which had a composition of 80 wt % $Cr_1Sb_2W_1Ox/10$ wt % $Al_2O_3$–10 wt % $SiO_2$. The reaction was carried out in the same manner as Example 1, except that the reaction temperature was raised to 540° C. The result was as shown in Table 1.

EXAMPLE 3

The fed amounts of chromium nitrate, aqueous ammonium metatungstate solution MW-2 and $Sb_2O_3$ were changed to 11.46 g, 19.92 g and 12.47 g, respectively, and a catalyst was prepared by a method otherwise identical with the one employed in Example 1, which had a composition of 80 wt % $Cr_1Sb_3W_{1.5}Ox/10$ wt % $Al_2O_3$–10 wt % $SiO_2$. The reaction was carried out in the same manner as Example 1, except that the reaction temperature was raised to 540° C. The result was as shown in Table 1.

EXAMPLE 4

A catalyst was prepared by a method identical with the one employed in Example 1, except that after addition of the aqueous ammonium metatungstate solution and before addition of the $Sb_2O_3$ dispersion, 0.351 g of ammonium metavanadate ($NH_4VO_3$, special grade reagent manufactured by Wako Junyaku) as dissolved in 50 ml of water under heating was added. The catalyst had a composition of 80 wt % $Cr_1Sb_{1.5}W_{0.5}V_{0.05}Ox/10$ wt % $Al_2O_3$–10 wt % $SiO_2$. The reaction was carried out in the identical manner with Example 1. The result was as shown in Table 1.

EXAMPLE 5

A catalyst was prepared by a method identical with the one employed in Example 2, except that after addition of the aqueous ammonium metatungstate solution and before addition of the $Sb_2O_3$ dispersion, 0.337 g of ammonium metavanadate as dissolved in 50 ml of water under heating was added. The catalyst had a composition of 80 wt % $Cr_1Sb_2W_1V_{0.07}Ox/10$ wt % $Al_2O_3$–10 wt % $SiO_2$. The reaction was carried out in the identical manner with Example 2. The result was as shown in Table 1.

EXAMPLE 6

A catalyst was prepared in identical manner with Example 5, except that 1.816 g of niobium oxalate (made by CBMM, containing 20.5 wt % as $Nb_2O_5$) as dissolved in 100 ml of water under heating was used instead of the ammonium metavanadate solution. The catalyst had a composition of 80 wt % $Cr_1Sb_2W_1Nb_{0.07}Ox/10$ wt % $Al_2O_3$–10 wt % $SiO_2$. The reaction was carried out in the identical manner with Example 2. The result was as shown in Table 1.

EXAMPLE 7

A catalyst was prepared by a method identical with the one employed in Example 1, except that 1,200 g of ammonium paramolybdate [$(NH_4)_6Mo_7O_{24}.4H_2O$, special grade reagent manufactured by Wako Junyaku) as dissolved in 50 ml of water under heating was added after addition of the aqueous ammonium metatungstate solution but before addition of the $Sb_2O_3$ dispersion. The catalyst had a composition of 80 wt % $Cr_1Sb_{1.5}W_{0.5}Mo_{0.05}Ox/10$ wt % $Al_2O_3$–10 wt % $SiO_2$. The reaction was carried out in the identical manner with Example 1. The result was as shown in Table 1.

EXAMPLE 8

A catalyst was prepared in the identical manner with Example 7, except that the ammonium paramolybdate was replaced by 0.861 g of manganese nitrate [$Mn(NO_3)_2.6H_2O$, special grade reagent manufactured by Wako Junyaku] as dissolved in 50 ml of water under heating. The catalyst had a composition of 80 wt % $Cr_1Sb_{1.5}W_{0.5}Mn_{0.05}Ox/10$ wt % $Al_2O_3$–10 wt % $SiO_2$. The reaction was conducted in the manner identical with Example 1. The result was as shown in Table 1.

EXAMPLE 9

A catalyst was prepared in the manner identical with Example 7, except that the ammonium paramolybdate was replaced by 1.212 g of iron nitrate [$Fe(NO_3)_3.9H_2O$, special grade reagent manufactured by Wako Junyaku] as dissolved in 50 ml of water under heating. The catalyst had a composition of 80 wt % $Cr_1Sb_{1.5}W_{0.5}Fe_{0.05}Ox/10$ wt % $Al_2O_3$–10 wt % $SiO_2$. The reaction was conducted in the manner identical with Example 1. The result obtained was as shown in Table 1.

EXAMPLE 10

A catalyst was prepared in the manner identical with Example 1 except that the fed amounts of the Silica Sol Snowtex N, chromium nitrate, aqueous ammonium metatungstate solution MW-2 and $Sb_2O$ were changed to 46.4 g, 14.13 g, 16.38 g and 7.73 g, respectively. The catalyst had a composition of 60 wt % $Cr_1Sb_{1.5}W_1Ox/10$ wt % $Al_2O_3$–30 wt % $SiO_2$. The reaction was carried out in the manner identical with Example 1. The result was as shown in Table 1.

EXAMPLE 11

A catalyst was prepared in the manner identical with Example 1 except that no silica sol was added and the fed amounts of the chromium nitrate, aqueous ammonium metatungstate solution MW-2 and $Sb_2O_3$ were changed to 22.86 g, 13.24 g and 16.67 g, respectively. The catalyst had a composition of 90 wt % $Cr_1Sb_2W_{0.5}Ox/10$ wt % $Al_2O_3$. The reaction was carried out in the manner identical with Example 2. The result was as shown in Table 2.

EXAMPLE 12

A catalyst was prepared in the manner identical with Example 2 except that no alumina sol was used and the fed amount of the Silica Sol Snowtex N was changed to 30.9 g. The catalyst had a composition of 80 wt % $Cr_1Sb_2W_1Ox/20$ wt % $SiO_2$. The reaction was carried out in the manner identical with Example 2. The result was as shown in Table 2.

EXAMPLE 13

A catalyst was prepared in the manner identical with Example 1, except that 3.17 g of anatase-form $TiO_2$ (first grade reagent manufactured by Wako Junyaku) was further added in powder form to the mixture of the alumina sol and silica sol, which had been stirred under heating and maintained at about 80° C.; and that the fed amounts of the chromium nitrate, aqueous ammonium metatungstate solution MW-2 and $Sb_2O_3$ were changed to 16.49 g, 19.11 g and 9.02 g, respectively. The catalyst had a composition of 70 wt % $Cr_1Sb_{1.5}W_1Ox$/10 wt % $Al_2O_3$–10 wt % $SiO_2$–10 wt % $TiO_2$. The reaction was carried out in the manner identical with Example 1. The result was as shown in Table 2.

EXAMPLE 14

A 300-ml beaker was charged with 16.50 g of chromium nitrate as dissolved in 50 ml of water and 19.11 g of the aqueous ammonium metatungstate solution MW-2, by the order stated. Then 12.03 g of $Sb_2O_3$ as dispersed in 100 ml of water in a homogenizer was added, followed by stirring under heating. To the system as being maintained at about 80° C., 6.35 g of $ZrO_2$ (Mitsuwa Kagaku Yakuhin; purity: 99.9%) in powder form was added, followed by stirring for 2 hours while the temperature of about 80° C. and the liquid amount of the system were maintained. Then the heating temperature was raised to 90° C. and the stirring was continued, whereby the system was concentrated for about 2 hours by evaporating the water content off. The subsequent drying and calcining were conducted similarly to Example 1, and a catalyst having the composition of 80 wt % $Cr_1Sb_2W_1Ox$/20 wt % $ZrO_2$ was obtained. The reaction was carried out in the manner identical with Example 2. The result was as shown in Table 2.

EXAMPLE 15

A catalyst was prepared in the manner identical with Example 14 except that no $ZrO_2$ was used and that the fed amounts of the aqueous ammonium tungstate solution MW-2 and $Sb_2O_3$ were changed to 9.56 g and 6.02 g, respectively. The catalyst had a composition of 100 wt % $Cr_1Sb_1W_{0.5}Ox$. The reaction was carried out in the manner identical with Example 1. The result was as shown in Table 2.

EXAMPLE 16

A catalyst was prepared in the manner identical with Example 14, except that no $ZrO_2$ was used, the fed amount of the aqueous ammonium metatungstate solution MW-2 was changed to 9.56 g and that the final calcining temperature was changed to 600° C. The catalyst had a composition of 100 wt % $Cr_1Sb_2W_{0.5}Ox$.

The reaction was carried out in the manner identical with Example 2. The result was as shown in Table 2.

Comparative Example 1

A catalyst was prepared in the manner identical with Example 1, except that no ammonium metatungstate was used and that the fed amounts of chromium nitrate and $Sb_2O_3$ were changed to 26.47 g and 19.30 g, respectively. The catalyst had a composition of 80 wt % $Cr_1Sb_2Ox$/10 wt % $Al_2O_3$–10 wt % $SiO_2$. The reaction was carried out in the manner identical with Example 2. The result was as shown in Table 3.

Comparative Example 2

A catalyst was prepared in the manner identical with Example 1, except that no $Sb_2O_3$ was used and that the fed amounts of chromium nitrate and the aqueous ammonium metatungstate solution MW-2 were changed to 32.98 g and 38.20 g, respectively. The catalyst had a composition of 80 wt % $Cr_1W_1Ox$/10 wt % $Al_2O_3$–10 wt % $SiO_2$. The reaction was carried out in the manner identical with Example 2. The result was as shown in Table 3.

Comparative Example 3

A catalyst was prepared in the manner identical with Example 1, except that no chromium nitrate was used and that the fed amounts of the aqueous ammonium metatungstate solution MW-2 and $Sb_2O_3$ were changed to 30.48 g and 9.59 g, respectively. The catalyst had a composition of 80 wt % $Sb_1WOx$/10 wt % $Al_2O_3$–10 wt % $SiO_2$. The reaction was carried out in the manner identical with Example 2. The result was as shown in Table 3.

Comparative Example 4

A catalyst was prepared in the manner identical with Example 1, except that the fed amounts of chromium nitrate, the aqueous ammonium metatungstate solution MW-2 and $Sb_2O_3$ were changed to 7.35 g, 8.51 g and 18.74 g, respectively. The catalyst had a composition of 80 wt % $Cr_1Sb_7W_1Ox$/10 wt % $Al_2O_3$–10 wt % $SiO_2$. The reaction was carried out in the manner identical with Example 2. The result was as shown in Table 3.

Comparative Example 5

A catalyst was prepared in the manner identical with Example 1, except that the fed amounts of chromium nitrate, the aqueous ammonium metatungstate solution MW-2 and $Sb_2O_3$ were changed to 6.94 g, 32.16 g and 7.59 g, respectively. The catalyst had a composition of 80 wt % $Cr_1Sb_3W_4Ox$/10 wt % $Al_2O_3$–10 wt % $SiO_2$.

The reaction was carried out in the manner identical with Example 2. The result was as shown in Table 3.

Comparative Example 6

A catalyst was prepared in the manner identical with Example 4, except that the fed amount of the ammonium metavanadate was changed to 1.05 g. The catalyst had a composition of 80 wt % $Cr_1Sb_{1.5}W_{0.5}V_{0.15}Ox$/10 wt % $Al_2O_3$–10 wt % $SiO_2$. The reaction was carried out in the manner identical with Example 1. The result was as shown in Table 3.

EXAMPLE 17

The reaction was carried out using the same catalyst as the one used in Example 4. The composition of the reaction gas was i-$C_4H_{10}$/$NH_3$/$O_2$/He/$H_2O$=1/2/4/7.5/3 (molar ratio), the space velocity SV was 900 hr$^{-1}$, and the reaction temperature was 470° C. Consequently, isobutane conversion of 72.2%, selectivity for methacrylonitrile of 30.4% and one pass yield of methacrylonitrile of 21.9% were obtained.

TABLE 1

| Example No. | Catalyst Composition | Carrier Component[1] | Reaction Temp. (°C.) | Propane Conversion (%) | Selectivity AN[2] | Selectivity $C_3'$[3] | Selectivity HCN[4] | One pass yield AN[2] | One pass yield AN + $C_3'$[5] |
|---|---|---|---|---|---|---|---|---|---|
| 1  | 80 wt. % $Cr_1Sb_{1.5}W_{0.5}Ox$         | A | 520 | 82.3 | 42.5 | 3.7 | 7.9 | 35.0 | 38.0 |
| 2  | 80 wt. % $Cr_1Sb_2W_1Ox$                 | A | 540 | 83.4 | 46.4 | 4.1 | 8.1 | 38.7 | 42.1 |
| 3  | 80 wt. % $Cr_1Sb_3W_{1.5}Ox$             | A | 540 | 79.7 | 37.8 | 4.9 | 7.0 | 30.1 | 34.0 |
| 4  | 80 wt. % $Cr_1Sb_{1.5}W_{0.5}V_{0.05}Ox$ | A | 520 | 84.0 | 48.8 | 3.2 | 8.7 | 41.0 | 43.7 |
| 5  | 80 wt. % $Cr_1Sb_2W_1V_{0.07}Ox$         | A | 540 | 86.2 | 46.5 | 3.1 | 9.1 | 40.1 | 42.8 |
| 6  | 80 wt. % $Cr_1Sb_2W_1Nb_{0.07}Ox$        | A | 540 | 84.5 | 46.4 | 4.0 | 8.2 | 39.2 | 42.6 |
| 7  | 80 wt. % $Cr_1Sb_{1.5}O_{0.5}Mo_{0.05}Ox$| A | 520 | 86.0 | 42.4 | 3.7 | 8.6 | 36.5 | 39.6 |
| 8  | 80 wt. % $Cr_1Sb_{1.5}W_{0.5}Mn_{0.05}Ox$| A | 520 | 84.5 | 42.3 | 3.8 | 8.0 | 35.7 | 39.0 |
| 9  | 80 wt. % $Cr_1Sb_{1.5}W_{0.5}Fe_{0.05}Ox$| A | 520 | 86.1 | 41.8 | 2.5 | 8.2 | 36.0 | 38.1 |
| 10 | 60 wt. % $Cr_1Sb_{1.5}W_1Ox$             | B | 520 | 83.8 | 40.8 | 4.0 | 8.7 | 34.2 | 37.5 |

[1] Carrier components in catalyst:
A = 10 wt. % $Al_2O_3$ – 10 wt. % $SiO_2$
B = 10 wt. % $Al_2O_3$ – 30 wt. % $SiO_2$
[2] AN: acrylonitrile
[3] $C_3'$: propylene
[4] HCN: hydrogen cyanide
[5] AN + $C_3'$: sum of acrylonitrile and propylene

TABLE 2

| Example No. | Catalyst Composition | Carrier Component[1] | Reaction Temp. (°C.) | Propane Conversion (%) | Selectivity AN[2] | Selectivity $C_3'$[3] | Selectivity HCN[4] | One pass yield AN[2] | One pass yield AN + $C_3'$[5] |
|---|---|---|---|---|---|---|---|---|---|
| 11 | 90 wt. % $Cr_1Sb_2W_{0.5}Ox$   | C | 540 | 82.1 | 42.0 | 2.9 | 7.8 | 34.5 | 36.9 |
| 12 | 80 wt. % $Cr_1Sb_2W_1Ox$       | D | 540 | 73.3 | 39.8 | 3.9 | 8.1 | 29.2 | 32.0 |
| 13 | 70 wt. % $Cr_1Sb_{1.5}W_1Ox$   | E | 520 | 83.1 | 38.0 | 4.2 | 7.7 | 31.6 | 35.1 |
| 14 | 80 wt. % $Cr_1Sb_2W_1Ox$       | F | 540 | 67.2 | 43.2 | 4.0 | 9.1 | 29.0 | 31.7 |
| 15 | 100 wt. % $Cr_1Sb_1W_{0.5}Ox$  | — | 520 | 59.6 | 49.8 | 4.4 | 8.9 | 29.7 | 32.3 |
| 16 | 100 wt. % $Cr_1Sb_2W_{0.5}Ox$  | — | 540 | 51.4 | 52.1 | 3.0 | 9.3 | 26.8 | 28.3 |

[1] Carrier components in catalyst:
C = 10 wt. % $Al_2O_3$
D = 20 wt. % $SiO_2$
E = 10 wt. % $Al_2O_3$ – 10 wt. % $SiO_2$ – 10 wt. % $TiO_2$
F = 20 wt. % $ZrO_2$
[2] AN: acrylonitrile
[3] $C_3'$: propylene
[4] HCN: hydrogen cyanide
[5] AN + $C_3'$: sum of acrylonitrile and propylene

TABLE 3

| Comparative Example No. | Catalyst Composition | Carrier Component[1] | Reaction Temp. (°C.) | Propane Conversion (%) | Selectivity AN[2] | Selectivity $C_3'$[3] | Selectivity HCN[4] | One pass yield AN[2] | One pass yield AN + $C_3'$[5] |
|---|---|---|---|---|---|---|---|---|---|
| 1 | 80 wt. % $Cr_1Sb_2Ox$                  | A | 540 | 60.5 | 14.9 | 3.4  | 2.6  | 9.0  | 11.1 |
| 2 | 80 wt. % $Cr_1W_1Ox$                   | A | 540 | 75.3 | 13.7 | 2.8  | 2.2  | 10.3 | 12.4 |
| 3 | 80 wt. % $Sb_1W_1Ox$                   | A | 540 | 16.4 | 14.1 | 38.2 | 3.1  | 2.3  | 8.6  |
| 4 | 80 wt. % $Cr_1Sb_7W_1Ox$               | A | 540 | 22.9 | 20.2 | 35.0 | 10.5 | 4.6  | 12.6 |
| 5 | 80 wt. % $Cr_1Sb_3W_4Ox$               | A | 540 | 62.4 | 23.5 | 6.3  | 4.0  | 14.7 | 18.6 |
| 6 | 80 wt. % $Cr_1Sb_{1.5}W_{0.5}V_{0.15}Ox$ | A | 520 | 92.4 | 19.8 | 0.6  | 4.2  | 18.3 | 18.8 |

[1] Carrier components in catalyst: A = 10 wt. % $Al_2O_3$ – 10 wt. % $SiO_2$
[2] AN: acrylonitrile
[3] $C_3'$: propylene
[4] HCN: hydrogen cyanide
[5] AN + $C_3'$: sum of acrylonitrile and propylene

We claim:

1. A method for the preparation of (meth)acrylonitrile by an ammoxidation process in which at least one saturated hydrocarbon selected from the group consisting of propane and isobutane is catalytically oxidized with a mixed gas containing molecular oxygen and ammonia in the presence of a catalyst, wherein the catalyst comprises a complex oxide expressed by the general formula (I)

$$Cr_\alpha Sb_\beta W_\gamma O_x \qquad (I)$$

wherein

α, β and γ denote the number of atoms of Cr, Sb and W, respectively, and when α is 1, β is 0.5–5 and γ is 0.2–2, and x is a value determined by the valances of the existing elements, and said catalyst contains, concurrently with the constituent elements of the complex oxide as expressed by the general formula (I), (i) at least one element selected from the group consisting of Nb, Mo, Mn, Fe, Co and Ni, in such an amount that the atomic ratio of the selected element or elements to Cr is 0 or exceeds 0 but is not more than 0.1, or (ii) at least one element selected from the group consisting of V, Nb, Mo, Mn, Fe, Co and Ni, in such an amount that the atomic ratio of the selected element or elements to Cr is 0 or exceeds 0 but is not more than 0.1 and the atomic ratio of the selected element or elements to Sb is 0 or exceeds 0 but is not more than 0.04.

2. The method as described in claim 1, wherein said catalyst is supported on a refractory inorganic carrier substance.

* * * * *